United States Patent
Warren et al.

(10) Patent No.: US 10,219,740 B2
(45) Date of Patent: Mar. 5, 2019

(54) SYSTEMS, METHODS AND APPARATUSES FOR THE ALLEVIATION AND OUTCOME MONITORING OF SLEEP DISORDERED BREATHING

(71) Applicant: HALARE, INC., Warriors Mark, PA (US)

(72) Inventors: Anthony C. Warren, Warriors Mark, PA (US); Kyle H. Goldschmidt, Saint Louis Park, MN (US)

(73) Assignee: Halare, Inc., Warriors Mark, PA (US)

( * ) Notice: Subject to any disclaimer, the term of this patent is extended or adjusted under 35 U.S.C. 154(b) by 26 days.

(21) Appl. No.: 15/124,418

(22) PCT Filed: Mar. 13, 2015

(86) PCT No.: PCT/US2015/020386
§ 371 (c)(1),
(2) Date: Sep. 8, 2016

(87) PCT Pub. No.: WO2015/138860
PCT Pub. Date: Sep. 17, 2015

(65) Prior Publication Data
US 2017/0172494 A1 Jun. 22, 2017

Related U.S. Application Data
(60) Provisional application No. 61/952,177, filed on Mar. 13, 2014.

(51) Int. Cl.
*A61B 5/00* (2006.01)
*A61B 5/08* (2006.01)
(Continued)

(52) U.S. Cl.
CPC .......... *A61B 5/4818* (2013.01); *A61B 5/0205* (2013.01); *A61B 5/0826* (2013.01);
(Continued)

(58) Field of Classification Search
CPC ... A61B 5/4818; A61B 5/7275; A61B 5/4833; A61B 5/4848; A61B 5/0205; A61B 5/113; A61B 5/14542; A61B 5/02405
See application file for complete search history.

(56) References Cited

U.S. PATENT DOCUMENTS 5,275,159 A 1/1994 Griebel
5,513,646 A * 5/1996 Lehrman ............... A61B 5/0205
128/903

(Continued)

FOREIGN PATENT DOCUMENTS

GB 2537574 A 10/2016
WO WO 2003/061471 7/2003
(Continued)

OTHER PUBLICATIONS

International Preliminary Report on Patentability for International Application No. PCT/US2015/020386, dated Sep. 13, 2016, 3 pages.
(Continued)

*Primary Examiner* — Michael W Kahelin
(74) *Attorney, Agent, or Firm* — RatnerPrestia

(57) ABSTRACT

Systems and methods for determining the effectiveness of breath training regimens are disclosed. The systems include a sensor assembly configured to detect data indicative of at least one physiological parameter of a user during breath training sessions while the user is awake and while the user is asleep. The system also includes an electronic computing unit with a processor configured to analyze the data indicative of the at least one physiological parameter of the user detected by the sensor assembly, and determine effectiveness of the breath training sessions on the user by determining trends of the at least one physiological parameter of the user from the analyzed data, and determining changes in the
(Continued)

at least one physiological parameter of the user while the user is asleep occurring during a period of time from the determined trends.

19 Claims, 4 Drawing Sheets

(51) Int. Cl.
  *A61B 5/0205* (2006.01)
  *G06F 19/00* (2018.01)
  *A61B 5/024* (2006.01)
  *A61B 5/11* (2006.01)
  *A61B 5/145* (2006.01)
  *A61B 5/113* (2006.01)

(52) U.S. Cl.
  CPC .......... *A61B 5/4833* (2013.01); *A61B 5/4848* (2013.01); *A61B 5/7275* (2013.01); *G06F 19/00* (2013.01); *A61B 5/024* (2013.01); *A61B 5/02405* (2013.01); *A61B 5/11* (2013.01); *A61B 5/113* (2013.01); *A61B 5/14542* (2013.01)

(56) References Cited

U.S. PATENT DOCUMENTS

| | | | |
|---|---|---|---|
| 7,942,824 B1* | 5/2011 | Kayyali | A61B 5/021 |
| | | | 128/204.23 |
| 8,249,686 B2 | 8/2012 | Libbus et al. | |
| 2005/0058456 A1 | 3/2005 | Yoo | |
| 2008/0312548 A1 | 12/2008 | Hartley et al. | |
| 2010/0175699 A1 | 7/2010 | Varney et al. | |
| 2011/0006901 A1* | 1/2011 | Cassidy | A61B 5/14551 |
| | | | 340/573.1 |
| 2011/0190594 A1* | 8/2011 | Heit | A61M 21/00 |
| | | | 600/301 |
| 2013/0131465 A1* | 5/2013 | Yamamoto | A61B 5/7271 |
| | | | 600/301 |
| 2013/0185097 A1 | 7/2013 | Saria et al. | |
| 2013/0237778 A1 | 9/2013 | Rouquette | |

FOREIGN PATENT DOCUMENTS

| | | | |
|---|---|---|---|
| WO | WO 2006/116469 | | 11/2006 |
| WO | WO 2009/036327 | | 3/2009 |
| WO | WO 2012/014691 | * | 2/2012 |
| WO | 2014100381 A1 | | 6/2014 |
| WO | 2015/138861 | | 9/2017 |

OTHER PUBLICATIONS

International Search Report and Written Opinion for PCT/US2015/020386 dated May 7, 2015.
International Search Report and Written Opinion for PCT/US2015/020388 dated Apr. 29, 2015.
Non Final Office Action for U.S. Appl. No. 15/124,424, dated Mar. 12, 2018, 15 pages.
Great Britain Examination Report for Application No. GB1617174.6, dated Mar. 9, 2018, 4 pages.
Non Final Office Action for U.S. Appl. No. 15/303,126, dated Apr. 27, 2018, 12 pages.
Great Britain Examination Report for GB Application No. 1617174.6, dated Oct. 5, 2018—3 pages.
Great Britain Examination Report for GB Application No. 1617174.6, dated Aug. 13, 2018, 2 pages.
Final Office Action for U.S. Appl. No. 15/303,126, dated Dec. 12, 2018, 29 pages.
Great Britain Examination Report for GB1617174.6, dated Nov. 19, 2018, 1 page.
German Communication and Examination Report for German Application No. 11 2015 001 216.8, dated Nov. 14, 2018 with translation, 10 pages.

* cited by examiner

SYSTEMS, METHODS AND APPARATUSES FOR THE ALLEVIATION AND OUTCOME MONITORING OF SLEEP DISORDERED BREATHING

CROSS-REFERENCE TO RELATED APPLICATIONS

This application is the U.S. national phase application of PCT International Application No. PCT/US2015/020386 filed Mar. 13, 2015, which claims priority to U.S. Provisional Application No. 61/952,177 entitled "Systems, Methods, and Apparatuses for the Alleviation and Outcome Monitoring of Sleep Disordered Breathing" filed on Mar. 13, 2014, the contents of each are incorporated fully herein by reference.

FIELD OF THE INVENTION

The present invention relates to breath training and detection of breath training effectiveness.

BACKGROUND OF THE INVENTION

A significant portion of sleep disordered breathing is a condition characterized by repeated episodes during sleep resulting in many detrimental and detectable effects on a person. Research has shown that sleep disordered breathing can have major short term and long term deleterious impacts. Therefore, there exists a need for improved and accessible systems and methods for detecting sleep disordered breathing in persons and providing instructions or regimens to improve sleep disordered breathing in persons.

SUMMARY OF THE INVENTION

Aspects of the invention include systems for monitoring sleep disordered breathing in a user. The system includes a sensor assembly configured to detect data indicative of at least one physiological parameter of a user during breath training sessions while the user is awake and while the user is asleep. The system also includes an electronic computing unit with a processor configured to analyze the data indicative of the at least one physiological parameter of the user detected by the sensor assembly, and determine effectiveness of the breath training sessions on the user by determining trends of the at least one physiological parameter of the user from the analyzed data, and determining changes in the at least one physiological parameter of the user while the user is asleep occurring during a period of time from the determined trends. The system also includes an output unit configured to provide information to the user regarding the effectiveness of the breath training regimen.

Further aspects of the invention include methods for monitoring sleep disordered breathing in a user. The method includes detecting, with a sensor assembly, data indicative of at least one physiological parameter of a user during breath training sessions while the user is awake and while the user is asleep. The method also includes analyzing, with a processor in an electronic computing unit, the data indicative of the at least one physiological parameter of the user detected by the sensor assembly, determining, with the processor, effectiveness of the breath training sessions by determining trends of the at least one physiological parameter of the user from the analyzed data, and determining changes in the at least one physiological parameter of the user while the user is asleep occurring during a period of time from the determined trends. The method further includes providing, with an output unit, information to the user regarding the determined effectiveness of the breath training sessions.

BRIEF DESCRIPTION OF THE DRAWINGS

The invention is best understood from the following detailed description when read in connection with the accompanying drawings, with like elements having the same reference numerals. When a plurality of similar elements is present, a single reference numeral may be assigned to the plurality of similar elements with a capital letter designation referring to specific elements. Included in the drawings are the following figures.

DETAILED DESCRIPTION OF THE INVENTION

Figure 1:
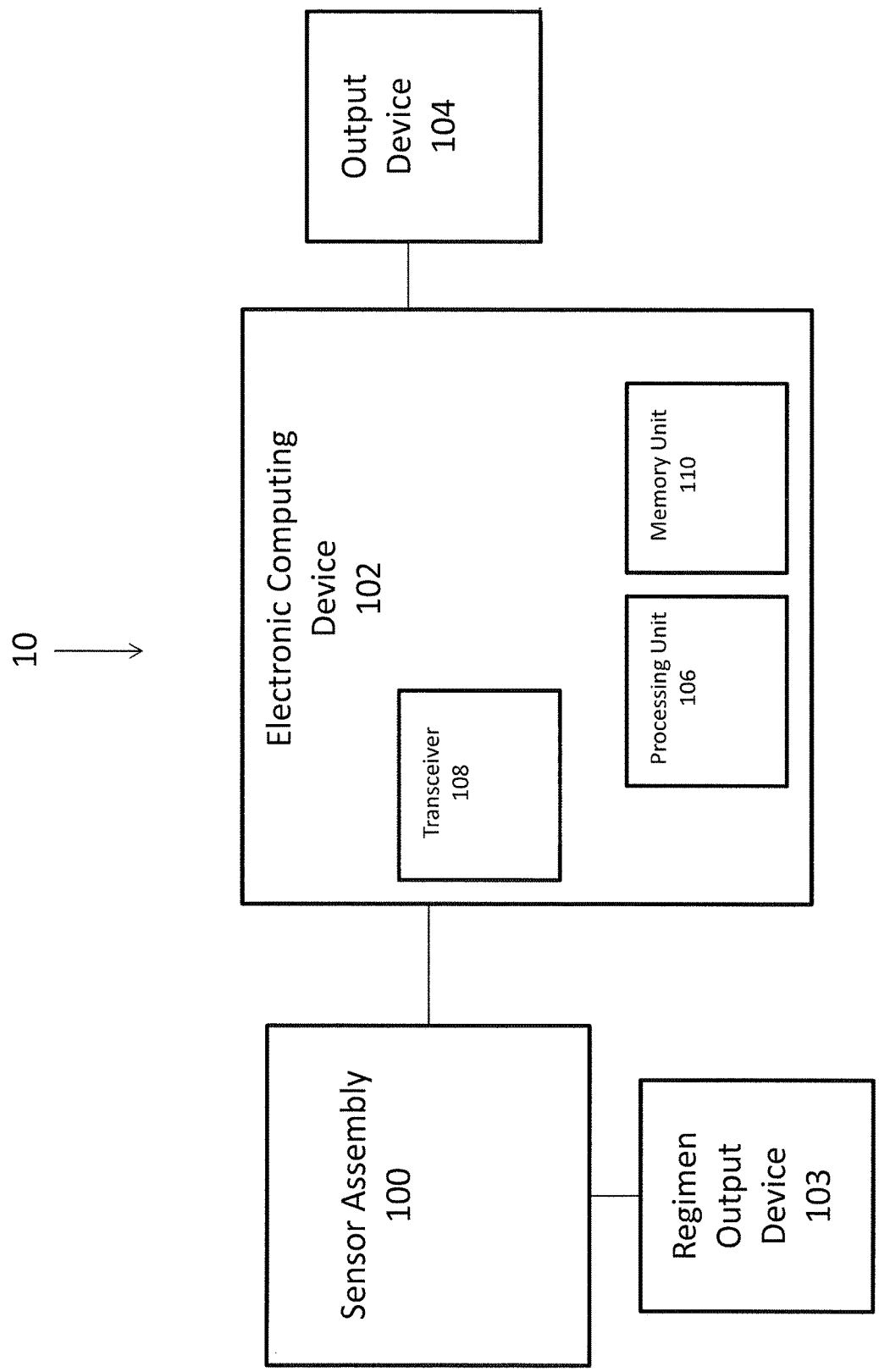
FIG. 1 is a block diagram of a system for determining the effectiveness of breath training according to aspects of the invention.

Referring to FIG. 1, a block diagram of a system 10 for monitoring sleep disordered breathing (SDB) and for determining effectiveness of breath training regimens according to aspects of the invention. The system 10 includes a sensor assembly 100, an electronic computing device 102, and an output device 104. Although the sensor assembly 100, the electronic computing device 102, and output device 104 are depicted as separate components in system 10, it is contemplated that any or all of these components may be integrated together in two or one device. For example, the sensor assembly, the electronic computing device 102, and the output device 104 may be integrated into an apparatus attachable to a user (e.g., a wristband, a neckband, other attachments, etc.), or in a smart device, such as a smart phone, tablet computer, laptop computer, etc.

The sensor assembly 100 includes at least one sensor that is configured to detect physiological data of the user that can be used to detect sleep disordered breathing (SDB) of the user. The sensor assembly 100 may include, for example, an accelerometer, a blood oxygen saturation sensor, a motion sensor, an audio sensor, a heart rate sensor, a breath sensor, a position sensor, etc. Other suitable sensors for detecting physiological data of a user will be understood by one of ordinary skill in the art from the description herein.

As referred to herein, a "user" is a person or persons or other entity undergoing treatment for sleep disordered breathing, wherein the treatment preferably includes breath training sessions. During breath training sessions, the user may receive instructions.

Figure 2B:
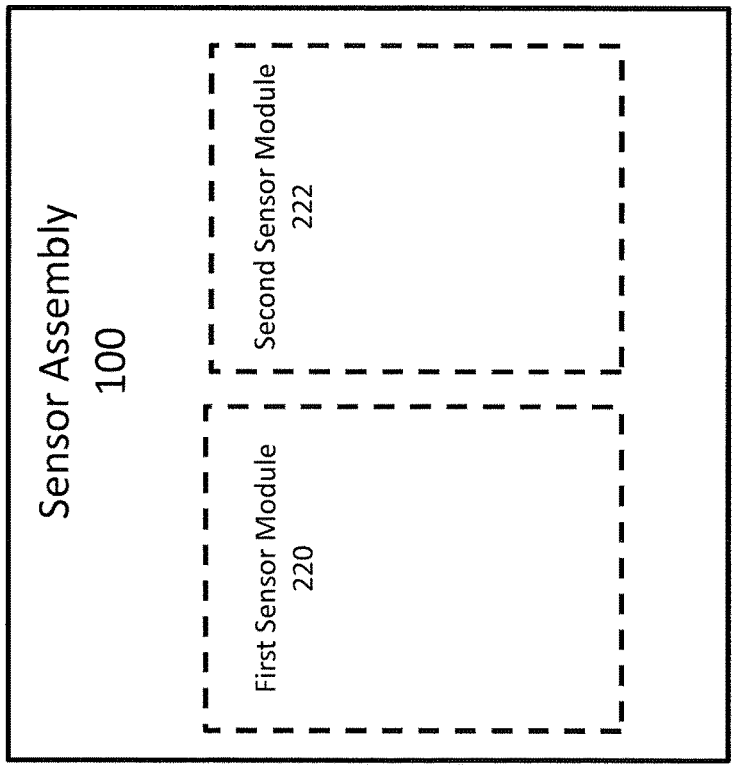
FIGS. 2A and 2B are block diagram depicting sensor assemblies in accordance with aspects of the invention.
Figure 2A:
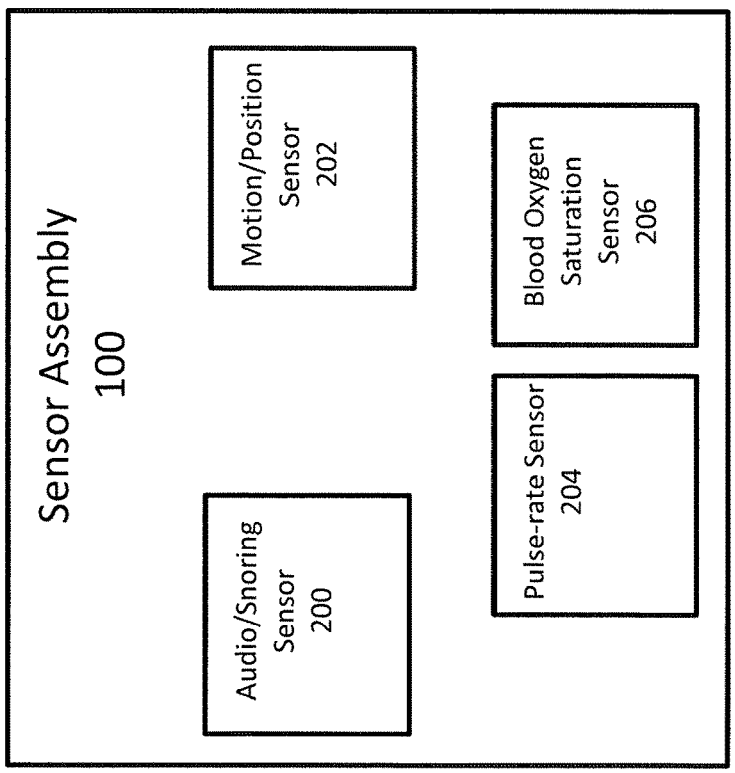

Referring to FIG. 2A, a diagram of an example of a sensor assembly 100 is shown. Although the sensor assembly 100 is shown with multiple sensors, the sensor assembly 100 may include only one of the sensors, or any combination of the sensors shown. In one embodiment, the sensor assembly 100 includes an audio/snoring sensor 200 adapted to detect snoring sounds from the user. The snoring sensor 200 may be adapted to detect time intervals between snoring sounds of the user and to detect the intensity of snoring from the user. Analysis of the physiological data in the form of intervals of snoring sounds and intensity of snoring sounds may be used to differentiate between apneic users suffering from Obstructive Sleep Apnea (OSA) and benign persons. Detection of snoring sounds is useful to determine whether a user has a history of snoring, whether snoring is an indication of possible SDB or is generally benign, whether the snoring is an indication of OSA, where in the user airway constrictions are occurring, etc.

The sensor assembly 100 may also include a position/movement sensor 202. In one embodiment, the position/movement sensor 202 is adapted to detect restlessness in sleep of the user as an indicator of periods of apnea or hypopnea in a user. In one example, OSA symptoms often exacerbate when the user lies on their back. Periods of excessive movement of the user during sleep may also be detected by the position/movement sensor 202, such that timing and intensity of the restlessness of the user may be analyzed to detect sleep disordered events for further analysis.

The sensor assembly 100 may also include a pulse-rate sensor 204 for detecting the heart rate of the user during sleep. The pulse-rate sensor 204 may be configured to detect periods of elevated pulse rate of the user during sleep, as well as disturbed or erratic pulse rates of the user as sleep disordered events, which may be used for further analysis.

A blood oxygen saturation ($O_2$sat) sensor 206 may also be included in the sensor assembly 100. In an embodiment, the $O_2$sat sensor 206 is adapted to detect changes in oxygen concentration levels of the user's blood during sleep as potential sleep disordered events.

FIG. 2B depicts an example of a sensor assembly 100 that includes a first sensor module 220 and a second sensor module 222. The first sensor module 220 and second sensor module 222 may be integrated into a single sensor apparatus, or may be integrated into separate components. In one embodiment, the first sensor module 220 includes sensors that are adapted to detect physiological data from a user during breath training sessions while the user is awake, and the second sensor module 222 includes sensors that are adapted to detect sleep disordered breathing of the user while the user is asleep. Each of the sensor modules 220 and 222 may include one or any combination of sensors such as those described above.

Referring back to FIG. 1, the system 10 includes a regimen output device 103. The regimen output device 103 is adapted to output instructions to the user according to the breath training regimen established for the user to detect physiological data of the user while the user is awake. The regimen output device 103 may be coupled to the sensor assembly 100, or may be a separate component, such as a smart phone, tablet computer, laptop computer, or other communication device capable of providing breath training instructions to the user.

The system 10 further includes an electronic computing device 102 with a processing unit 106, a transceiver 108, and a memory unit 110. The transceiver 108 may be utilized to receive physiological data detected from the sensor assembly 100. In embodiments where the electronic computing device 102 is integrated with the sensor assembly 100, the transceiver 108 may not be a necessary component for the transmission and reception of data to be analyzed by the electronic computing device 102. The memory unit 110 is depicted as integrated into the electronic computing device 102. It is contemplated that additional memory units may be utilized, such as a memory unit integrated into the sensor assembly 100 or a cloud storage device. Such memory units are configured to store detected physiological data and subsequent analyzed data.

The processing unit 106 is adapted to process the data detected by the sensor assembly 100 according to particular algorithms to detect sleep disordered events, determine whether sleep disordered events are indicative of SDB symptoms, detect physiological data from the user produced in response to a breath training regimen, and to determine the effectiveness of the breath training regimen on the user based on the detection of sleep disordered events.

The particular algorithms the processing unit 106 applies to the physiological data detected by the sensor assembly 100 depends upon the type of data detected and the sensors that are used to detect the data. Although the algorithms described herein are related to an individual sensor type, the physiological data analyzed from each type of sensor may be used in conjunction with or in combination with data from other sensors to detect sleep disordered events, and develop trends of the user over time to determine effectiveness of a breath training regimen on the user.

In examples where the sensor assembly 100 includes an audio/snoring sensor, such as sensor 200, the processing unit 106 may apply algorithms as follows. Baselines may be established for time intervals between snoring of the user and intensity of the snoring for the user. The processing unit 106 receives the snoring physiological data and tracks the snoring of the user. When the snoring sensor 200 records snoring occurrences of the user that occur within a time interval that exceeds the time interval baseline, the processing unit 106 determines that the exceeding of the baseline is a sleep disordered event. Alternatively, the time interval baseline may be established such that the processing unit 106 determines a sleep disordered event if snoring occurrences of the user occur too quickly within one another. Similarly, the audio level of the snoring (e.g., a decibel level) may be indicative of intensity of the snoring of the user. A baseline may be established such that when the audio level of a snoring occurrence of the user exceeds the baseline, the intensity of such snoring occurrence may be determined to be a sleep disordered event by the processing unit 106.

In order to record audible snoring sounds with sufficient fidelity to enable the analysis, the sound sensor 200 may be mounted closer to the face of the user, using, as one example, a microphone near the throat. In this case, the sound sensor 200 may be in a separate sensor module apparatus which communicates either by wire, or preferably wirelessly, to either the wrist mounted module, or directly to an electronic computing apparatus for subsequent analysis as described above. This method increases the fidelity of the audible sound detection by reducing interference say from another snorer nearby, or by a wrist mounted sound detector being physically obscured from the user's head.

In examples where the sensor assembly 100 includes a motion or position sensor 202, baselines may be established against which the physiological data from the motion/position sensor 202 is analyzed with the processing unit 106. Amounts of motion or changes of position of the user during sleep are detected by the motion/position sensor 202. When the amounts of motion or changes of position exceed the established baselines, the processing unit 106 determines that the amount of motion or change of position can be a sleep disorder event. Data from the sensor 202 are analyzed using a rolling average and periods of extensive movement from an established resting baseline and lasting more than 10 seconds indicate periods of restlessness the timing and intensity of which are stored together with the time stamp for subsequent correlation. Similarly, position orientation is also stored with a time stamp for subsequent correlation.

Similarly with a pulse rate sensor 204, the processing unit 106 may be adapted to detect heart rate variability (HRV) in the user during sleep. Analysis techniques, such as converting R-R data sets into frequency domain using Fast Fourier Transform algorithms can derive HRV and the time when the power and frequency spectrum of the HRV change. In addition, longer periods of significantly disturbed or erratic HRV may indicate periods of an intensive series of apnea or hypopnea events. The times, amplitudes, and other associated parameters analyzed from the pulse rate sensor 204 may be used for later correlation analysis.

When an $O_2$sat sensor is used, the data detected may be analyzed using a rolling average to seek reductions in the index from a baseline value. Then the processing unit 106 may use a Nervus Algorithm (NA) to extract further detail from the initially determined indications of the occurrence of an apnea or hypopnea event. Typically desaturation is considered to have commenced as soon as the oxygen concentration level falls below the baseline by a specified amount, say by 2% and continues until the signal recovers to a second level which is lower than the baseline by a further 25% of the first determined baseline value. This algorithm defines different levels of drop for desaturation (drop gap) and re-saturation (return gap). This removes any errors that may be associated in assuming the pre- and post-saturation levels are the same. Indeed, often the post-event level lies below the pre-event value.

Figure 3:
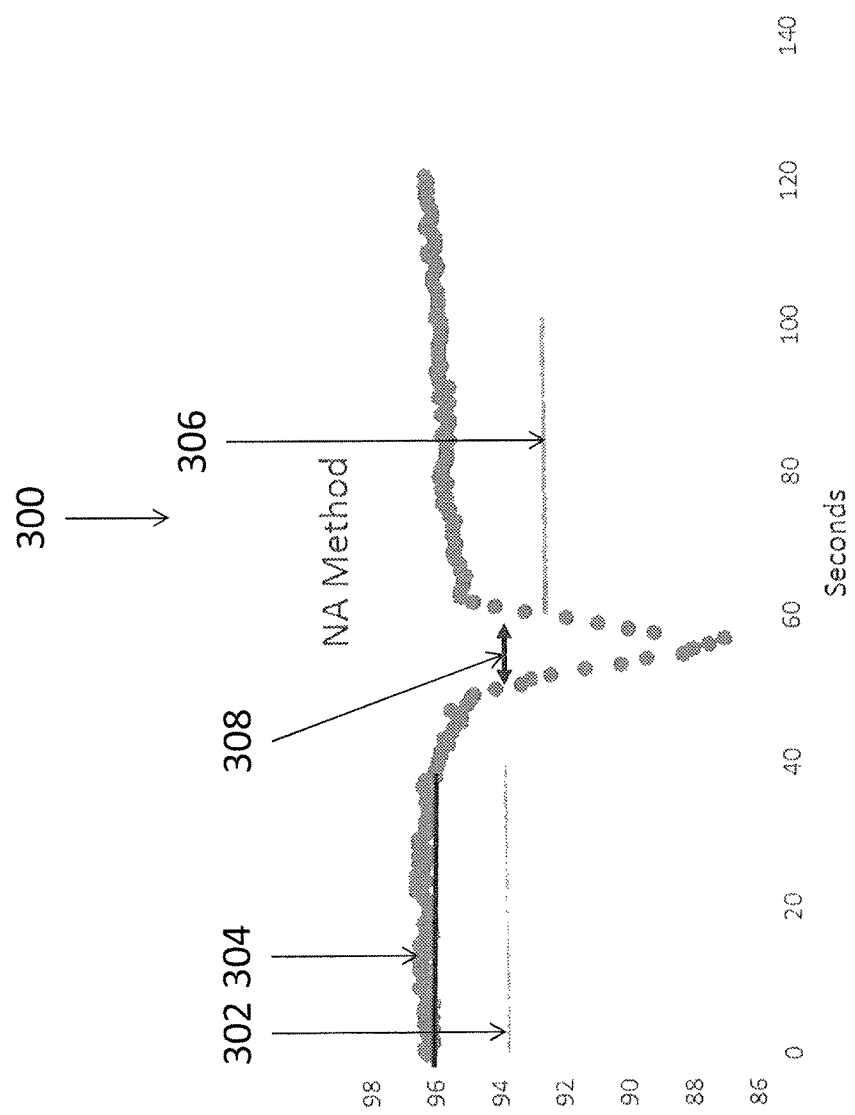
FIG. 3 is a chart depicting data indicative of desaturation in accordance with aspects of the invention.

The NA method is shown in the chart 300 of FIG. 3. In this example, the drop gap 302 is arbitrarily taken as 2% below the pre-event baseline 304 and the line 306 is the post-event base-line level which is an additional 0.2% below the pre-event baseline. For this event, the time interval of standard desaturation shown by the double-headed arrow 308, and the lowest value of $O_2$sat are recorded. Together they characterize the severity of the apnea event. The desaturation time span and the depth of desaturation for each event are stored together with the time stamp for subsequent correlation.

Thus, the data detected from the sensor assembly 100 may be analyzed by the processing unit 106 in conjunction with each sensor of the sensor assembly 100. Prior to analysis, the data may be pre-processed to remove outliers and long-term trends. Using rolling averaging algorithms on the results of the pre-processed data, periods of brachycardia are determined. The times when such brachycardia events are detected may be used for later correlation analysis.

Further analysis may include, for example, analyzing data from the snoring sensor 200 in conjunction with data from the motion/position sensor 202 to more reliable determine whether a sleep disordered event is caused by a symptom of SDB or is merely benign. More than one indication of a sleep disordered event or symptoms of SDB may be detected in embodiments where multiple or different types of sensors are used in sensor assembly 100. Correlation between more than one indication of a sleep disordered event improves the overall accuracy of the measurements, thereby reducing both Type I and Type II errors.

Along with each data point detected from the sensors of the sensory assembly 100, the system 10 may also include an electronic clock to associate times along with the physiological data detected by the sensor assembly 100. Thus, time signatures can be associated with each data point, which allows for better correlation between data detected from multiple sensors in the sensor assembly 100. In one example, data from an audio sensor (e.g., audio sensor 200) is analyzed using wavelet bi-coherence methods to determine whether periods of snoring are more likely to result from obstructive sleep apnea rather than being benign. The intensity and time span of the snoring events together with their time stamp of occurrence are used for subsequent correlation.

The results of the analysis conducted by the processing unit 106 are subjected to one or more known statistical methods for multivariate data analysis such as so-called principal components, factor, cluster, and discriminant techniques. The correlation of data from multiple independent sensors, each of which has singly demonstrated the ability to diagnose apnea and hypopnea symptoms, significantly reduces errors of both Type I and Type II.

Advantageously, the systems, methods, and apparatus disclosed herein allow for correlation between multiple types of physiological data detected to increase the reliability of the data, reduce the appearance of errors in the data, and more effectively diagnose sleep disordered breathing by determining whether a sleep disordered event is benign or is indicative of a sleep disordered symptom.

In one example, an accelerometer is used to detected restlessness of a user. The restlessness may be detected as compared with a baseline stationary posture ΔR (e.g., non-movement) and may be detected according to an amount of time of restlessness tΔR.

In another example, a blood oxygen saturation sensor is used to detect a period of oxygen desaturation from a pre-determined baseline. A baseline may be, for example, defined as for X seconds below Y % of oxygen saturation. Times of a sleep disordered event from the blood oxygen saturation sensor tSp may be determined from desaturation or oxygen concentration of the blood of the user.

A microphone or audio sensor may also be used to detect snoring sounds. Data detected from a microphone may include amount of snoring sounds, length of snoring events, frequency components, intensity, loudness compared with non-snoring episodes, etc. In one example for loudness compared with non-snoring episodes, three levels of sound (e.g., greater than 30 dB, greater than 40 dB, greater than 50 dB) may be used, and each time the level of sound that occurs from a snoring event exceeds one, or any of the levels of sound $t\Delta Sn_{1,2,3}$ are recorded.

Position of the user may also be detect, where the time the user is laying on his or her back tB is detected and recorded as physiological data for later correlation and analysis.

In another example, a pulse-rate sensor is used to detect variation in interbeat intervals. As described above, this physiological data can be used to determine heartrate variability (HRV). The times where the HRV increases from a pre-determined baseline tΔHR are used for correlation and analysis.

The above described physiological data may be detected from the sensor assemblies and then correlated with each other to determine whether a sleep disordered event is indicative of a sleep disordered symptom or is benign. For example, when a snoring event tΔSn is detected that exceeds a baseline level, if it is also detected that the position tB of the user is that of the user laying on his or her back, the detected snoring event is likely benign. Furthermore, if the snoring event is coupled without blood oxygen saturation tSp outside of the baseline and/or without HRV tΔHR outside of the baseline, then the correlation of the data would indicate that the snoring event is benign. The data from the position sensor, the blood oxygen saturation sensor, and the pulse rate sensor may be correlated with the data from the audio sensor to indicate that a snoring event is benign.

Other events outside of snoring may be indicative of sleep disordered breathing symptoms. For example, when the physiological data indicates that tΔHR for HRV exceeds the baseline along with the tSp for blood oxygen levels exceeding the baseline, the system determines that the event detected by tΔHR is that of a sleep disordered breathing event. In another example, when the time of restlessness tΔR exceeds the baseline stationary posture ΔR, but occurs without a registered snoring event tΔSn and/or with the position sensor indicating that the user is not laying on his or her back, the system determines that the event detected by tΔR is indicative of a sleep disordered breathing event.

The systems, methods, and apparatus may also detect co-morbidity of sleep disordered events and snoring events. For example, when a snoring event is detected tΔSn along with a HRV event tΔHR, and/or an oxygen saturation event tSp, and/or a restlessness event tΔR, co-morbidity of snoring and sleep disordered events may exist.

These data points and correlation of data may be utilized to develop trends of the user over time. For example, trends of desaturation, snoring, HRV events, restlessness events, etc., may be mapped over a predetermined amount of time. These trends may then be utilized to determine effectiveness of a breath training regimen regarding whether the breath training regimen is successful in reducing or eliminating SDB of the user over time.

Thus, the user may utilize the first sensor module that is configured to detect physiological data of the user while the user is awake and is undertaking breath training sessions. The first sensor module may be attached to the user at a location where such physiological data may be detected. Such locations include but are not limited to the ear lobe, ear canal, wrist, ankle, upper arm, neck, etc. The physiological data detected by the first sensor module is indicative of data associated with the correct production as a result of the breath training regimen. Once detected, the data is stored and/or transmitted to the electronic computing device for further analysis. Such analysis may include determining compliance with the regimen, effectiveness of the regimen, etc.

The second sensor module is adapted to detect physiological data of the user while the user is asleep. It will be understood that the first sensor module and second sensor module may be separate units, or may be integrated into the same unit. The data detected by the second sensor module is utilized to determine whether sleep disordered breathing by the user is occurring, and the data may be analyzed and correlated as described above to determine whether sleep disordered breathing is occurring.

Accordingly, once the data is detected and analyzed by the second sensor module, trends of the user's breathing over time can be determined. These trends determine the effectiveness of the breath training regimen over time by showing whether certain sleep disordered breathing events are increasing or decreasing over time, whether the intensity or frequency of the sleep disordered events are increasing or decreasing over time, whether a certain type of sleep disordered breathing is occurring more or less frequently over time, etc. In an embodiment, the effectiveness of the breath training regimen is determined based on an increase or a decrease of sleep disordered breathing events.

Once the trends are established and the effectiveness of the breath training regimens are determined, the systems and methods disclosed herein may be utilized to determined particular treatments for the user and/or update the breath training regimen of the user. For example, the systems and methods may be utilized to update the breath training regimen and implement the new regimen/instructions on the sensor assembly.

The system 10 further includes an output device 104. The output device 104 is configured to output sleep disordered events, sleep disordered breathing symptoms, trends, and/or effectiveness determinations to a person in charge of care of the user (e.g., a doctor, a proctor of an experiment, etc.). The output device 104 may be any device capable of communicating information regarding the analyzed data to a user or other personnel, such as a display of a smart phone, tablet computer, laptop computer, etc. The output device 104 may also be configured to communicate instructions to the user for the breath training regimen. The output device 104 may also be adapted to transmit the information to a doctor, and provide suggested treatments for the user based on the analyzed data.

As one example illustrating how sensor derived information can be used to modify a breath training regimen, analyses of the output from the sensor assembly determine that the user suffers from chronic benign snoring but not SDB. The user is provided with a breath training regimen for alleviating benign snoring and the sensor module subsequently monitors length and intensity of snoring episodes during periods of sleep. The prescribed regimen is designed to be followed once daily for twenty minutes for a period of twelve weeks in order to reduce both the length and intensity of the snoring episodes by at least 90%. This reduction may also follow a known trend such as a power law asymptotic curve to the anticipated final snoring levels after twelve weeks, or an exponential trend line that intercepts with the 90% reduction line after twelve weeks, or other known trend lines. After seven days, reduction of snoring intensity from the initial level of greater 50 dB indicates an improvement trend exceeding that anticipated, enabling a prediction to be made on the amount of breath training that will be effective. In such a case, the user is informed that they will be able to complete the regimen in ten weeks rather than twelve and a modified regimen is provided to the user. Alternatively, the user may undertake the breathing exercises in only two days out of every three sequential days and a modified regimen is provided to the user. Should the improvement in snoring levels indicate that the regimen must be extended to 14 weeks in order to meet the desired reduction in snoring levels, a longer regimen is provided. Feedback showing how compliance with the regimen can affect the length or periodicity of the regimen, provides significant encouragement for the user to be compliant and hence derive the anticipated benefits.

As another example illustrating how sensor derived information can be used to modify a breath training regimen, analyses of the output from the sensor assembly determine that the user suffers from SDB, specifically obstructive sleep apnea (OSA) and that the length of time of breathing interruptions lie in the range of 25-35 seconds. The user has been provided with a breath training regimen designed to reduce or eliminate apnea events of this length but is unable to complete the regimen which would take them beyond the level of 30 seconds. The sensor assembly detects an improvement in the number of apnea events but some apnea events still occur, usually beyond 30 seconds in length. The user requires a new breathing training regimen in order to raise their tolerance level of breathing interruptions without hyperventilating. In order to improve the outcomes, a new breath training regimen may for example focus initially on breathing control by gradually training for a lower breathing rate with more regularity. Once the user has attained adequate breathing control, the regimen will again be modified to gradually increase their tolerance for breathing interruption without resultant hyperventilation by providing prompts for exhale and/or inhale actions which increase marginally, say less than 0.25 seconds, with each daily or periodic exercise session. In this way the user first improves their breathing control capabilities before increasing their tolerance for interruption beyond the 35 seconds which the sensor module has shown to be their target. Other suitable trends analysis will be understood by those of skill in the art from the disclosure herein.

In another embodiment, information from a partner of the user may be utilized to determine the effectiveness of a breath training regimen. For example, a partner of the user will often be disturbed during sleep while sleep disordered events are occurring in the user. The partner may have interrupted sleep patterns, increased restlessness, increased heart rates, etc.

In one embodiment, the partner has access to a survey (e.g., an online survey) that includes a series of questions regarding the partner's sleep that is used by the electronic computing unit 102 as additional data regarding the effectiveness of the breath training regimen of the user. In another example, the partner utilizes a sensor device that includes sensors to detect data regarding the sleep of the partner (e.g., instances where the partner wakes up, etc.). This data may be correlated with sleep disordered events detected of the user to determine the intensity of the sleep disordered event. For example, if the sensor assembly 100 detects a sleep disordered event of the user during sleep, and the sensor of the partner indicates that, at the same time, the partner's sleep was interrupted, this data would indicate that the sleep disordered event is of sufficient severity to disrupt the sleep of the partner. Alternatively, if the partner's sleep is not interrupted upon the occurrence of the sleep disordered event, these data could indicate that the severity of the sleep disordered event has been reduced, thereby indicating that the sleep disordered event may have reduced in intensity due to the breath training regimen.

Figure 4:
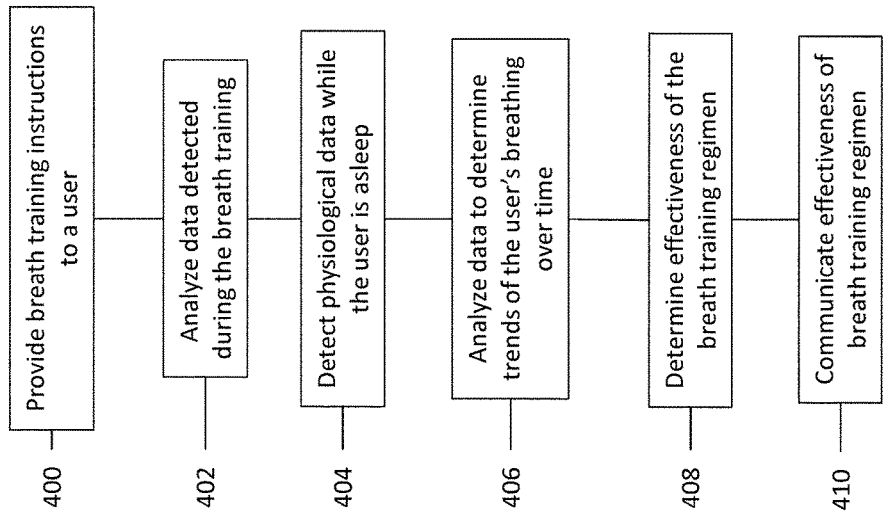
FIG. 4 is a flowchart of steps in a method for determining the effectiveness of breath training regimens in accordance with aspects of the invention.

FIG. 4 is a flowchart 40 of steps for determining the effectiveness of a breath training regimen over time in a user in accordance with aspects of the invention. At step 400, breath training instructions are provided to the user. The instructions may be output via, for example, a regimen output device 104. The instructions are designed to provide physiological data that are detected by a sensor assembly while the user is awake to assess compliance and effectiveness of the breath training regimen on the user. The data may be detected with a sensor assembly, such as sensor assembly 100. The data may include motion data, position data, audio data, heart rate data, blood oxygen saturation data, etc.

At block 402, the data are analyzed. The data may be analyzed by a processing unit, such as processing unit 106. The data are analyzed to determine compliance and trends of the user's breathing over time when the user is awake.

At block 404, physiological data is detected while the user is asleep to detect sleep disordered breathing events of the user. Sleep disordered breathing events may be determined by correlating data from multiple sensors. As described above, various sensors and physiological data may be correlated and/or otherwise combined to improve the accuracy of the diagnoses and differentiate between benign sleep disordered events and sleep disordered events that are indicative of sleep disordered breathing symptoms.

At block 406, the data collected at block 404 are analyzed and processed to establish trends of the user's sleep over time. The trends include trends of sleep disordered events over a predetermined period of time of the user.

At block 408, the effectiveness of the breath training regimen is determined. The effectiveness of the breath training regimen may be determined utilizing the trends established at block 406. The trends may indicate increases or decreases in the number of sleep disordered events and/or the intensity or severity of sleep disordered events over time. The breath training regimen is determined to be effective when the trends indicate improvement of sleep disordered breathing of the user over the time from the trend.

At block 410, the effectiveness of the trends are communicated and the breath training regimen may be updated and implemented on the user. The trends and updates may be communicated via a display on an output device, such as a mobile smart phone, tablet, or computer. The updates may be in the form of breathing instructions to the user. In an embodiment, the information is transmitted to a doctor or other personnel in charge of the care of the user, and the information may contain graphical representations of the detected data and indications of the sleep disordered events. The doctor may then determine different or additional breath training instructions/regimen for the user based on the trends and upload/update the breath training instructions/regimen to be implemented on the user.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for monitoring sleep disordered breathing, the system comprising:
    a sensor assembly configured to detect data indicative of at least one physiological parameter of a user during breath training sessions occurring while the user is awake, the breath training sessions including voluntary breath holding occurrences, and to detect data indicative of at least one physiological parameter obtained while the user is asleep,
    an electronic computing unit comprising:
    a processor configured to:
        analyze the data indicative of the at least one physiological parameter obtained by the sensor assembly while the user is asleep and the at least one physiological parameter of a user during the breath training sessions occurring while the user is awake,
        determine effectiveness of the breath training sessions occurring while the user is awake by:
            determining trends of the at least one physiological parameter obtained while the user is asleep from the analyzed data and determining trends of the voluntary breath holding occurrences obtained during the breath training session, and
            determining changes in the at least one physiological parameter obtained while the user is asleep during a period of time from the determined trends by determining a number of sleep disorder events occurring over the period of time and by determining if the frequency of the number of sleep disorder events is changing; and
    an output unit configured to provide, to the user, information regarding the determined effectiveness of the breath training sessions.

2. The system of claim 1, wherein the sensor assembly further comprises:

a first sensor module configured to detect the data indicative of at least one physiological parameter of the user during breath training sessions while the user is awake; and a second sensor module configured to detect the data indicative of at least one physiological parameter of the user while the user is asleep.

3. The system of claim 1, wherein the sleep disordered breathing includes at least one of apnea and hypopnea.

4. The system of claim 1, wherein the sensor assembly further comprises at least one of a pulse-rate sensor, a blood oxygen concentration sensor, and a motion sensor.

5. The system of claim 1, wherein the at least one physiological parameter of the user includes heart rate (HR), oxygen saturation ($O_2$Sat) of the user, and motion of the user's body while the user is asleep.

6. The system of claim 1, further comprising a transmitter coupled to the sensor assembly and configured to communicate the data indicative of at least one physiological parameter of the user from the sensor assembly to the electronic computing unit.

7. The system of claim 1, wherein in the determined trends include trends of at least one of Heart Rate Variability (HRV), periods of movement during sleep, involuntary apnea occurrences and hypopnea occurrences, and $O_2$Sat of the user.

8. The system of claim 1, wherein the determined changes include changes in at least one of Heart Rate Variability (HRV), voluntary breath holding occurrences, periods of movement during sleep, involuntary apnea occurrences and hypopnea occurrences, and $O_2$Sat of the user.

9. The system of claim 1, wherein the processor is further configured to determine, from at least one of the determined trends and the determined changes, at least one of:
the user's compliance with a prescribed regimen including the breath training sessions, existence of improvements for the user over time during the breath training sessions and while asleep in at least one of HRV, voluntary breath holding occurrences, periods of movement, involuntary apnea occurrences, involuntary hypopnea occurrences, and $O_2$Sat levels of the user, and
courses of action for reducing the user's symptoms and the sleep disordered breathing experienced by the user.

10. The system of claim 1, wherein the information provided to the user includes at least one of information about:
the user's compliance with a prescribed regimen including the breath training sessions, existence of improvements for the user over time during the breath training sessions and while asleep in at least one of HRV, voluntary breath holding occurrences, periods of movement, involuntary apnea occurrences, involuntary hypopnea occurrences, and $O_2$Sat levels of the user, and
courses of action for reducing the user's symptoms and the sleep disordered breathing experienced by the user.

11. The system of claim 2, wherein the second sensor module includes a motion sensor for detecting motion of the user's body while the user is asleep.

12. A method for monitoring sleep disordered breathing in a user, the method comprising the steps of:
detecting, with a sensor assembly, data indicative of at least one physiological parameter of a user during breath training sessions occurring while the user is awake, the breath training sessions including voluntary breath holding occurrences, and data indicative of at least one physiological parameter obtained while the user is asleep,
analyzing, with a processor in an electronic computing unit, the data indicative of the at least one physiological parameter obtained by the sensor assembly while the user is asleep and the at least one physiological parameter of a user during the breath training sessions occurring while the user is awake,
determining, with the processor, effectiveness of the breath training sessions occurring while the user is awake by:
determining trends of the at least one physiological parameter obtained while the user is asleep from the analyzed data and determining trends of the voluntary breath holding occurrences obtained during the breath training session, and
determining changes in the at least one physiological parameter obtained while the user is asleep during a period of time from the determined trends by determining a number of sleep disorder events occurring over the period of time and by determining if the frequency of the number of sleep disorder events is changing; and
providing, with an output unit, information to the user regarding the determined effectiveness of the breath training sessions.

13. The method of claim 12, wherein the method further comprises the step of determining from at least one of the determined trends and the determined changes, with the processor, at least one of:
the user's compliance with a prescribed regimen including the breath training sessions, existence of improvements for the user over time during the breath training sessions and while asleep in at least one of HRV, voluntary breath holding occurrences, periods of movement, involuntary apnea occurrences, involuntary hypopnea occurrences, and $O_2$Sat levels of the user, and
courses of action for reducing the user's symptoms and the sleep disordered breathing experienced by the user.

14. The method of claim 12, wherein the method further comprises the step of detecting, with the processor, occurrences and severity of at least one of involuntary apnea events and involuntary hypopnea events, by combining two or more measurements derived from the data indicative of the at least one physiological parameter of the user.

15. The method of claim 12, wherein the method further comprises the step of detecting, with the processor, occurrences and severity of at least one of voluntary apnea events and voluntary hypopnea events, by combining two or more measurements derived from the data indicative of the at least one physiological parameter of the user.

16. The method of claim 12, wherein the information provided to the user includes at least one of information about:
the user's compliance with a prescribed regimen including the breath training sessions, existence of improvements for the user over time during the breath training sessions and while asleep in at least one of HRV, voluntary breath holding occurrences, periods of movement, involuntary apnea occurrences, involuntary hypopnea occurrences, and $O_2$Sat levels of the user, and
courses of action for reducing the user's symptoms and the sleep disordered breathing experienced by the user.

17. The method of claim 12, wherein the method further comprises the step of storing, with a memory unit, at least one of the data indicative of the at least one physiological parameter of the user detected by the sensor assembly, the analyzed data, and the determined effectiveness of the breath training sessions.

18. The method of claim 12, wherein the method further comprises the steps of: detecting, at a first sensor module incorporated into the sensor assembly, the data indicative of at least one physiological parameter of a user during breath training sessions while the user is awake; and detecting, at a second sensor module incorporated into the sensor assembly, the data indicative of at least one physiological parameter of a user while the user is asleep.

19. The method of claim 12, wherein the determining the effectiveness of the breath training regimen further comprises determining changes in sleep patterns in a person that sleeps in the vicinity of the user.

\* \* \* \* \*